(12) United States Patent
Arai et al.

(10) Patent No.: US 12,283,349 B2
(45) Date of Patent: Apr. 22, 2025

(54) METAGENOMIC ANALYSIS OF MICROBIAL FLORA

(71) Applicant: Varinos, Inc., Tokyo (JP)

(72) Inventors: Wataru Arai, Tokyo (JP); Yoshiyuki Sakuraba, Tokyo (JP); Yoko Nagai, Tokyo (JP)

(73) Assignee: VARINOS, INC., Tokyo (JP)

( * ) Notice: Subject to any disclaimer, the term of this patent is extended or adjusted under 35 U.S.C. 154(b) by 0 days.

(21) Appl. No.: 18/549,570

(22) PCT Filed: Dec. 15, 2021

(86) PCT No.: PCT/JP2021/046237
§ 371 (c)(1),
(2) Date: Sep. 7, 2023

(87) PCT Pub. No.: WO2022/190496
PCT Pub. Date: Sep. 15, 2022

(65) Prior Publication Data
US 2024/0296909 A1    Sep. 5, 2024

(30) Foreign Application Priority Data
Mar. 8, 2021  (JP) .................................. 2021-036093

(51) Int. Cl.
*G06F 16/00* (2019.01)
*G06F 18/232* (2023.01)
(Continued)

(52) U.S. Cl.
CPC .......... *G16B 40/00* (2019.02); *G06F 18/232* (2023.01); *G16B 30/00* (2019.02)

(58) Field of Classification Search
CPC .. G06F 16/785; G06F 16/7854; G06F 16/786; G06F 16/7867; G06F 18/23213;
(Continued)

(56) References Cited

U.S. PATENT DOCUMENTS

2017/0114396 A1    4/2017   Chim et al.
2018/0105444 A1*   4/2018   Asako ................... G16B 40/20
(Continued)

FOREIGN PATENT DOCUMENTS

JP    2017519514 A    7/2017
JP    2018088843 A    6/2018

OTHER PUBLICATIONS

Moreno, I. et al., "Evidence that the endometrial microbiota has an effect on implantation success or failure," American Journal of Obstetrics and Gynecology, vol. 215, No. 6, Dec. 1, 2016, 20 pages.

(Continued)

*Primary Examiner* — Shyue Jiunn Hwa
(74) *Attorney, Agent, or Firm* — McCoy Russell LLP

(57) ABSTRACT

A method of the present invention includes: performing clustering on a sample sequence, the clustering including the following: grouping base sequences having 100% similarity with each other, for the sample sequences thereby to generate a primary OTU (Operational Taxonomic Unit); and further performing the clustering on the sample sequences thereby to generate a secondary OTU composed of a sequence of a predetermined centroid, and sample sequences that have a similarity larger than or equal to a predetermined threshold value with the sequence of the centroid. Here, the predetermined threshold value is less than 100%. The method further includes: setting a sequence of a primary OTU having the largest number of sequences among the primary OTUs included in each secondary OTU, as a representative sequence of the secondary OUT; collating the representative sequence with a database; and thereby estimating a lineage of the secondary OTU.

11 Claims, 10 Drawing Sheets

(51) Int. Cl.
  *G16B 30/00* (2019.01)
  *G16B 40/00* (2019.01)
(58) Field of Classification Search
  CPC ........ G16B 20/00; G16B 40/00; G16B 40/20;
    G16B 20/20; G16B 25/00; G16B 30/00;
    C12Q 1/6869; C12Q 1/689; C12Q 1/04;
    A61K 35/76; A61K 45/06; C12N
    2795/00021; Y02A 50/30; C02F 2209/36
  See application file for complete search history.

(56) References Cited

U.S. PATENT DOCUMENTS

| | | | |
|---|---|---|---|
| 2019/0034588 A1 | 1/2019 | Mande et al. | |
| 2020/0227139 A1* | 7/2020 | Ravel | G16B 30/20 |
| 2021/0090694 A1* | 3/2021 | Colley | G16H 15/00 |
| 2021/0386796 A1* | 12/2021 | Nagler | A23L 33/135 |

OTHER PUBLICATIONS

Taiwan Patent Office, Office Action Issued in Application No. 111108165, Feb. 3, 2022, 7 pages. (Submitted with Machine Translation).

Japan Patent Office, Office Action Issued in Application No. 2021-036093, Mar. 8, 2022, 6 pages. (Submitted with Machine Translation).

ISA Japan Patent Office, International Search Report Issued in Application No. PCT/JP2021/046237, Mar. 8, 2022, WIPO, 4 pages.

Edgar, R., "Updating the 97% identity threshold for 16S ribosomal RNA OTUs," Bioinformatics, vol. 34, No. 14, Jul. 15, 2018, Available Online Feb. 28, 2018, 5 pages.

Kyono, K. et al., "Analysis of endometrial microbiota by 16S ribosomal RNA gene sequencing among infertile patients: a single-center pilot study," Reproductive Medicine and Biology, vol. 17, No. 3, May 6, 2018, Published Online Jul. 2018, 10 pages.

Kitaya, K. et al., "Characterization of Microbiota in Endometrial Fluid and Vaginal Secretions in Infertile Women with Repeated Implantation Failure," Mediators of Inflammation, vol. 2019, May 21, 2019, 11 pages.

Terrat, S. et al., "ReClustOR: a re-clustering tool using an open-reference method that improves operational taxonomic unit definition," Methods in Ecology and Evolution, vol. 11, No. 1, Jan. 2020, Available Online Oct. 14, 2019, 13 pages.

European Patent Office, Extended European Search Report Issued in Application No. 21930341.9, Feb. 24, 2025, Germany, 8 pages.

* cited by examiner

METAGENOMIC ANALYSIS OF MICROBIAL FLORA

CROSS REFERENCE TO RELATED APPLICATIONS

The present application is a U.S. National Phase of International Application No. PCT/JP2021/046237 entitled "METAGENOMIC ANALYSIS OF MICROBIAL FLORA," and filed on Dec. 15, 2021. International Application No. PCT/JP2021/046237 claims priority to Japanese Patent Application No. 2021-036093 filed on Mar. 8, 2021. The entire contents of each of the above-listed applications are hereby incorporated by reference for all purposes.

TECHNICAL FIELD

The present invention includes a metagenomic analysis of a microbial flora, and particularly includes a meta 16S ribosomal RNA (16S rRNA) analysis of a bacterial flora (hereinafter referred to as meta 16S analysis, in some cases).

BACKGROUND ART

Non-Patent Literature 1 shows that the microbial flora in the uterus, in particular, a bacterial flora (flora, microbiota, microbiome) in the uterus, gives influence on the success rate of in-vitro fertilization. Patent Literature 1 discloses methods of: specifically, PCR-amplifying the 16S rRNA gene in all genomic DNAs extracted from bacteria contained in the amniotic fluid, with the use of a universal primer for the 16S ribosomal RNA gene common to each bacterium; and further identifying a chorioamnionitis-associated microorganism by an analysis with the use of an Operational Taxonomic Unit (hereinafter referred to as OTU), and another analysis, for the amplified product. Patent Literature 2 discloses a method of determining the risk of a pregnant woman or a newborn, based on the bacterial taxa.

CITATION LIST

Patent Literature

Patent Literature 1: Japanese Unexamined Patent Application Publication No. 2018-088843
Patent Literature 2: Published Japanese Translation of PCT International Publication for Patent Application, No. 2017-519514

Non Patent Literature

Non Patent Literature 1: Inmaculada Moreno, Francisco M. Codoner, Felipe Vilella, Diana Valbuena, Juan F. Martinez-Blanch, Jorge Jimenez-Almazan, Roberto Alonso, Pilar Alama, Jose Remohi, Antonio Pellicer, Daniel Ramona and Carlos Simon, "Evidence that the endometrial microbiota has an effect on implantation success or failure", American Journal of Obstetrics and Gynecology, Dec. 1, 2016, Volume 215, Issue 6, p. 684 to 703

SUMMARY OF INVENTION

The inventors have devised a method for metagenomically analyzing the intrauterine microbial flora and other general microbial floras. Such an analysis method utilizes clustering based on a threshold value for the similarity between sequences.

In one example of the analysis method devised by the inventors, so-called exploratory clustering is used. In the exploratory clustering, a change of a cluster to which data is to be assigned and a change of a centroid (centroid) of the cluster are iterated. As one example, when there is no more change in the assignment of clusters, the processing ends there. The cluster at that time is defined as an OTU, and the centroid thereof is defined as a representative sequence (Representative Sequence). The representative sequence is collated with a database, and the organism species of the OTU is determined.

There is high possibility that such a representative sequence is often a pseudo sequence which is specifically a sequence that the microorganisms in the microbial flora do not actually have. Accordingly, there is a possibility that an error occurs in the determination for the OTU. An object of the present invention is to provide a means suitable for reducing an influence of the pseudo sequence, when the clustering is performed based on a threshold value for the similarity between sequences, in a metagenomic analysis of a microbial flora.

[1] A method of a metagenomic analysis of a bacterial flora includes:
performing clustering on base sequences obtained by DNA sequencing of a sample containing the bacterial flora, which will be hereinafter referred to as a sample sequence, wherein the clustering includes
grouping base sequences having 100% similarity with each other, for the sample sequences thereby to generate a primary OTU (Operational Taxonomic Unit), and
performing the clustering on the sample sequences thereby to generate a secondary OTU composed of a sequence of a predetermined centroid, and sample sequences that have a similarity larger than or equal to a predetermined threshold value with the sequence of the centroid, on condition that the predetermined threshold value is less than 100%; and
setting a sequence of a primary OTU having a largest number of sequences among the primary OTUs included in each secondary OTU, as a representative sequence of the secondary OTU, collating the representative sequence with a database, and thereby estimating a lineage of the secondary OTU.

[2] The method according to [1], further includes, at the time when generating the secondary OTU, iterating operations of:
firstly, assigning a cluster different from the primary OTUs to the sample sequences; and
further reassigning the cluster to a sample sequence having a similarity larger than or equal to a predetermined threshold value with the sequence of the centroid of the cluster,
until convergence.

[3] The method according to [2], wherein firstly assigning the cluster to the sample sequence comprises:
randomly selecting a seed sequence from the sample sequence; and
also assigning a first cluster to the seed sequence and a sequence having a similarity larger than or equal to the predetermined threshold value with the seed sequence.

[4] The method according to [2] or [3], wherein
when the secondary OTU is generated after the primary OTU has been created,
the cluster is a cluster including the primary OTU; and
the sequence of the centroid is an average obtained by weighting the sequences of the primary OTUs with the number of sequences of the primary OTUs.

[5] The method according to any one of [2] to [4], wherein when the cluster reassignment has been performed and an assignment
of all the clusters have not changed, it is determined that convergence occurs.
[6] The method according to any one of [1] to [5], wherein
the sample is an intra-uterine fluid or a vaginal swab of a subject; the sample sequence is generated by DNA sequencing of a partial sequence of a 16S rRNA gene of genomic DNAs extracted from the sample;
the database includes a sequence and an annotation of the 16S rRNA gene of genus *Lactobacillus;*
in the lineage estimation, a genus of a bacterium of the secondary OTU is estimated, and
data is generated which includes an identifier of the subject and a composition ratio of genera of bacteria containing the genus *Lactobacillus* in the bacterial flora.
[7] The method according to [6], wherein
the database further includes sequences and annotations of 16S rRNA genes of genus *Bifidobacterium,* genus *Propionibacterium,* genus *Gardnerella,* genus *Streptococcus,* and genus *Veillonella;* and
the partial sequence is a sequence of a portion in the whole sequences of the 16S rRNA genes, which is not completely conserved among these bacterial genera.
[8] The method according to [6] or [7], wherein
the database is a database generated by a meta-analysis of a plurality of other databases.
[9] A method for diagnosing ease of pregnancy of a subject includes:
collecting an intra-uterine fluid or a vaginal swab from the subject as a sample;
metagenomically analyzing the sample by the method according to any one of [1] to [5], wherein
the sample sequences are generated by DNA sequencing of a partial sequence of a 16S rRNA gene of genomic DNAs extracted from the sample, and
the database includes sequences and annotations of the 16S rRNA gene of genus *Lactobacillus;*
in the lineage estimation, estimating a genus of a bacterium of a secondary OTU; and
diagnosing ease of pregnancy of the subject, based on a composition ratio of genus *Lactobacillus* to genera of bacteria other than genus *Lactobacillus* in a bacterial flora.
[10] A method of a metagenomic analysis of a microbial flora of a eukaryote includes:
performing clustering on base sequences obtained by DNA sequencing of a sample containing the microbial flora, which will be hereinafter referred to as a sample sequence, wherein the clustering includes
grouping base sequences having 100% similarity with each other, for the sample sequences, thereby to generate a primary OTU (Operational Taxonomic Unit), and
performing the clustering on the sample sequences thereby to generate a secondary OTU composed of a sequence of a predetermined centroid, and sample sequences that have a similarity larger than or equal to a predetermined threshold value with the sequence of the centroid, on condition that the predetermined threshold value is less than 100%; and
setting a sequence of the primary OTU having a largest number of sequences among the primary OTUs included in each secondary OTU, as a representative sequence of the secondary OTU, collating the representative sequence with a database, and thereby estimating a lineage of the secondary OTU.
[11] A program for metagenomic analysis of a microbial flora of bacteria or eukaryotes, the program being configured to:
cause a computer to perform clustering on base sequences obtained by DNA sequencing of a sample containing the microbial flora, which will be hereinafter referred to as a sample sequence, wherein the clustering includes
grouping base sequences having 100% similarity with each other, for the sample sequences thereby to generate a primary OTU (Operational Taxonomic Unit), and
performing the clustering on the sample sequences thereby to generate a secondary OTU composed of a sequence of a predetermined centroid, and sample sequences that have a similarity larger than or equal to a predetermined threshold value with the sequence of the centroid, on condition that the predetermined threshold value is less than 100%; and
set a sequence of a primary OTU having a largest number of sequences among the primary OTUs included in each secondary OTU, as a representative sequence of the secondary OTU, causing the computer to collate the representative sequence with a database, and thereby causing the computer to estimate a lineage of the secondary OTU.

The present invention can provide a means suitable for reducing an influence of the pseudo sequence, when the clustering is performed based on a threshold value for the similarity between sequences, in a metagenomic analysis of a microbial flora.

DESCRIPTION OF EMBODIMENTS

In the present embodiment, a metagenomic analysis of a microbial flora, in particular, a bacterial flora, is performed. The metagenomic analysis utilizes non-hierarchical clustering, in particular, exploratory clustering. Due to the exploratory clustering being utilized, an accuracy of the clustering and a calculation cost can be balanced. One example of the exploratory clustering is k-means clustering (k-means).

Figure 1:
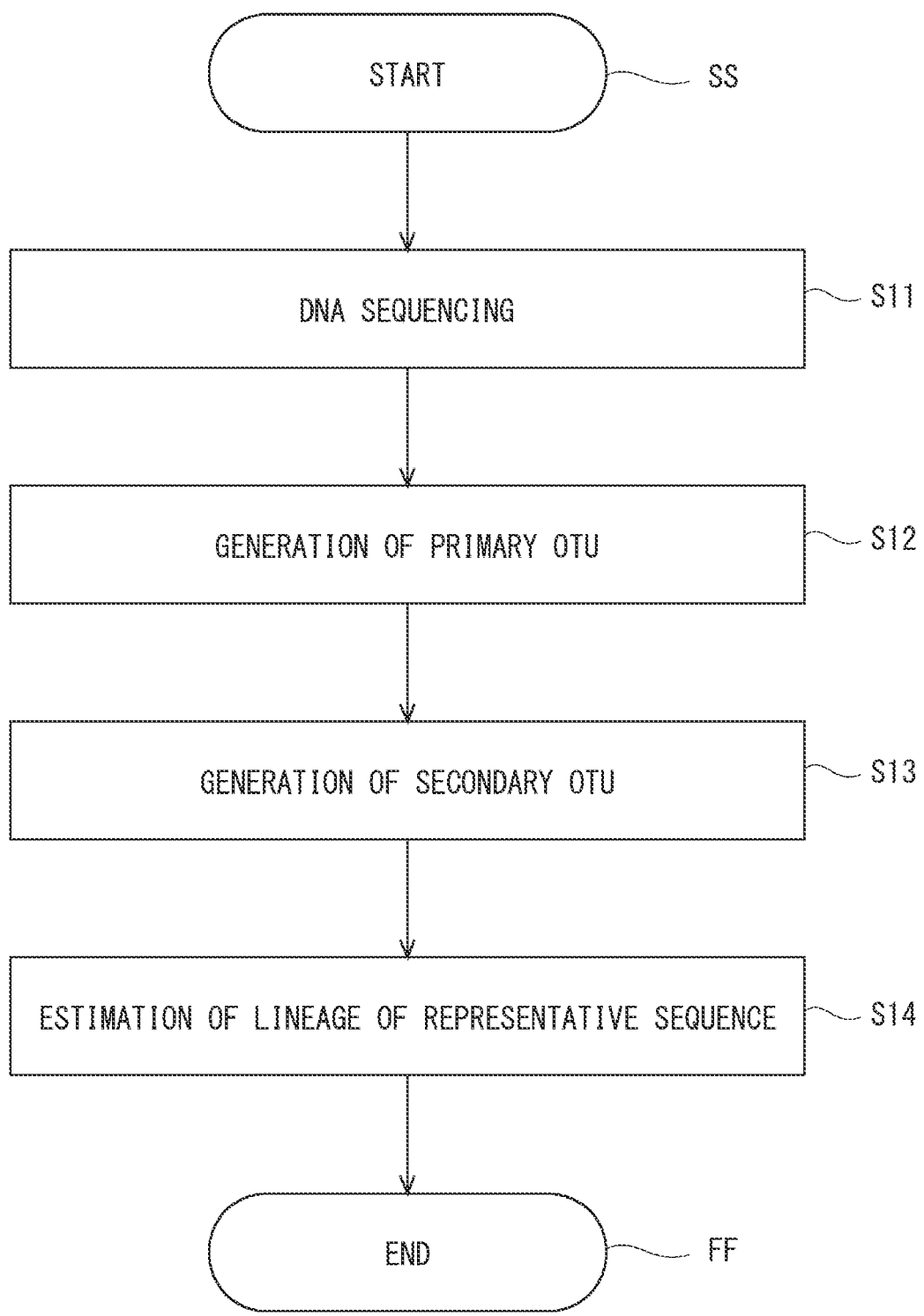
FIG. 1 is a flow of a metagenomic analysis.

FIG. 1 is a flow of the metagenomic analysis. Each processing of the metagenomic analysis is mechanically performed by a computer, and each processing may be shared by separate computers, or each processing may also be intensively performed by one computer. In step S11, a sample containing a bacterial flora is subjected to DNA sequencing, and a base sequence is obtained. Hereinafter, such a base sequence will be referred to as a sample sequence.

In one aspect, a bacterial flora is collected from any of the amniotic cavity, the uterine lumen, the endocervical canal and the vagina (vagina). In the present specification, the "vagina" is a medical term which is used as a word representing Vagina in English and German languages. In one aspect, a DNA to be a sample is extracted from any of: an endocervical swab, a vaginal swab (vaginal swab), a placental swab, and an umbilical cord swab; the urine, the amniotic fluid, the whole blood, the serum, the plasma, the intra-uterine fluid and the endocervical mucus; and tissues other than those.

In one aspect a DNA sequencer sends a sample sequence to a computer. A computer automatically processes the sample sequence. In another aspect, the DNA sequencer sends the sample sequence to a server which is connected thereto via a network. The server records the sample sequence. According to the request of the computer, the server sends the sample sequence to the computer which is connected thereto via the network. The computer automatically processes the sample sequence.

Next, in step S12 shown in FIG. 1, sample sequences are grouped by 100% similarity, and a primary OTU (Primary OTU) is obtained. In one aspect, the grouping is performed by exploratory clustering. Next, in step S13, the sample sequences are subjected to exploratory clustering at a threshold value for similarity less than 100%, and a secondary OTU (Secondary OTU) is obtained. Next, in step S14, a representative sequence in the secondary OTU is subjected to estimation of the lineage, and thereby, the lineage of the secondary OTU is estimated.

The term "OTU", specifically "Operational Taxonomic Unit" refers to a taxonomic unit of an organism, which is obtained when the base sequences of an organism are classified on a computer using their similarity as an index. When the organism is a bacterium, for example, the base sequence of 16S rRNA gene is used. One of important methods of using the OTU is to classify real organisms, for example, bacteria that constitute a bacterial flora, based on the OTU, regardless of whether the OTU coincides or not with the taxonomy of Linne or a taxonomic unit on the evolutionary taxonomy. On the other hand, it is possible to associate the OTU to the taxonomy of Linne or the taxonomic unit on the evolutionary taxonomy, by estimating the lineage of the OTU. It is easy to clinically use the information on the OTU of which the lineage has been estimated in this way.

In step S11 of FIG. 1, a sample sequence is obtained. The sample sequence is obtained as a set of base sequences that various types and lineages of bacteria have which are contained in the bacterial flora. The set of the sample sequences contains an abundance ratio of each genus of bacteria in a bacterial flora. In addition, individual sample sequences originate in any one genus or species. In one aspect, the lineage of the bacterium is not estimated at this time. In one aspect, the abundance ratio of each genus of bacteria in the bacterial flora is not estimated at this time.

The sample sequence is set so as to become a predetermined length, in view of the known genomic sequence. However, the lengths of the sample sequences do not necessarily completely coincide with each other, because the occurrence of deletion or duplication is taken into consideration, which includes a cause by an error in DNA sequencing. The sample sequence can be a genomic sequence in which the preserving property is low among species and the preserving property is high within the species. In one aspect, a fragment of a genomic DNA having a sample sequence is cloned with the use of, for example, a primer or an adapter.

Figure 2:
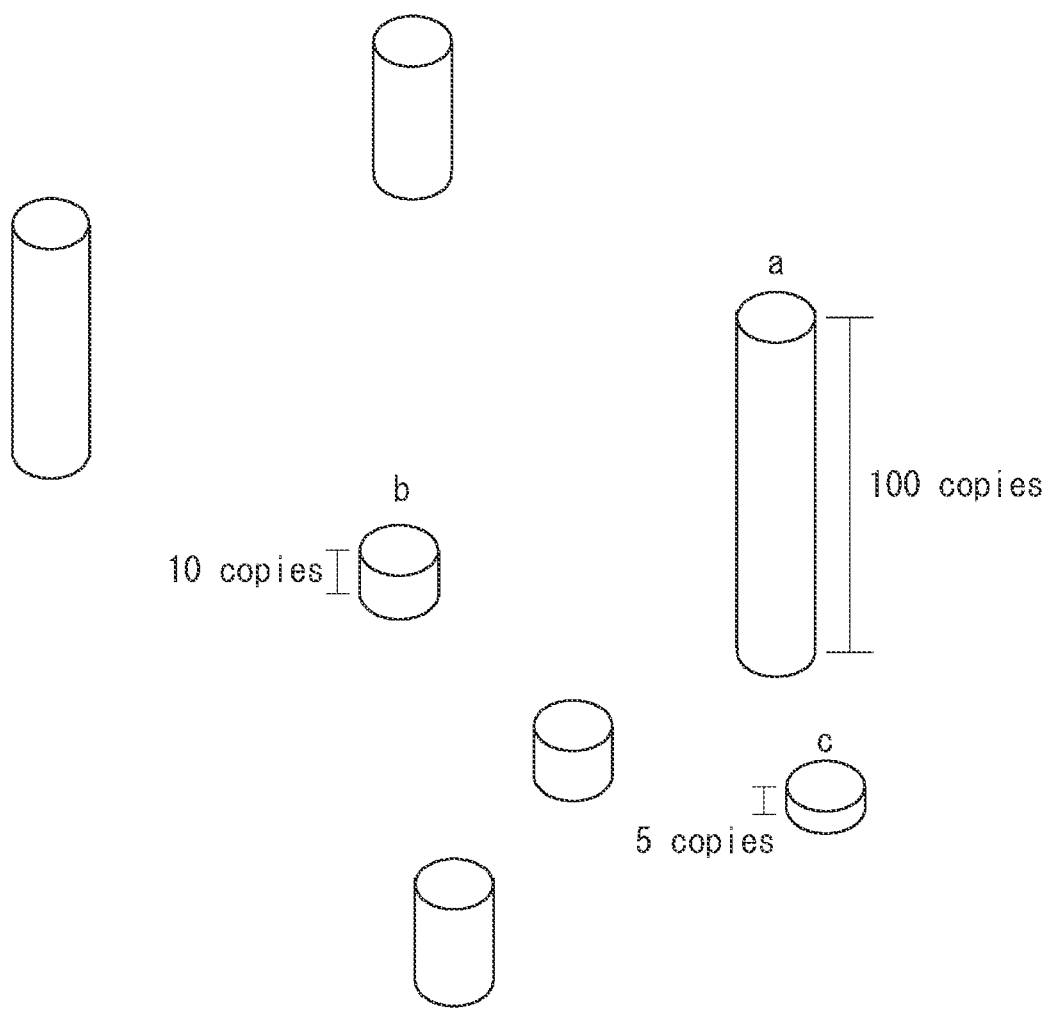
FIG. 2 is grouping according to 100% similarity.

FIG. 2 illustrates an example of a method of grouping base sequences having 100% similarity with each other, in the sample sequences. As shown in the upper part, an OTU a has 100 copies of, an OTU b has 10 copies of, and an OTU c has 5 copies of the sequence. In the sequence of the OTU b, substitution of two bases (from ATT to AGC) occurs with respect to the sequence of the OTU a. In the sequence of the OTU c, substitution of two bases (from ATT to TGT) occurs with respect to the OTU a. By this grouping, the primary OTU (Operational Taxonomic Unit) is generated. This grouping is equivalent to clustering at the threshold value of sequence similarity of 100%. The 100% similarity represents perfect coincidence of sequences in a predetermined length of the sample sequence.

Each column in the lower part of FIG. 2 represents each cluster; in other words, represents the primary OTU. The height of each column represents the number of copies of each primary OTU. The shorter the distance between each primary OTU, the higher the sequence similarity. Note that the figure is schematic, because the similarity of the sequence cannot be accurately represented on a two-dimensional plane.

In step S12 of FIG. 1, a relationship between the sequence of each primary OTU and the number of copies (Copy Number) of the sequence is revealed. Hereinafter, the number of copies of a sequence is referred to as the number of sequences, in some cases. In one aspect, a ratio between the numbers of sequences of the primary OTUs represents the abundance ratio of bacteria having these sequences in the bacterial flora. The same applies to other OTUs than the primary OTU. However, the term "number of copies" in this embodiment does not necessarily indicate that the individual sample sequences within the primary OTU and the other OTUs are homogeneous sequences obtained from bacteria having the same genome. There is a possibility that sequences other than the sample sequence on the genomic sequence are different between bacteria. Accordingly, it is presumed that the bacteria in the primary OTU are included in the taxonomic unit, species or genus.

In one aspect, after the primary OTU has been created, the secondary OTU is created. Thus, the exploratory clustering is performed according to the procedure shown in FIG. 3 to FIG. 6.

Figure 3:
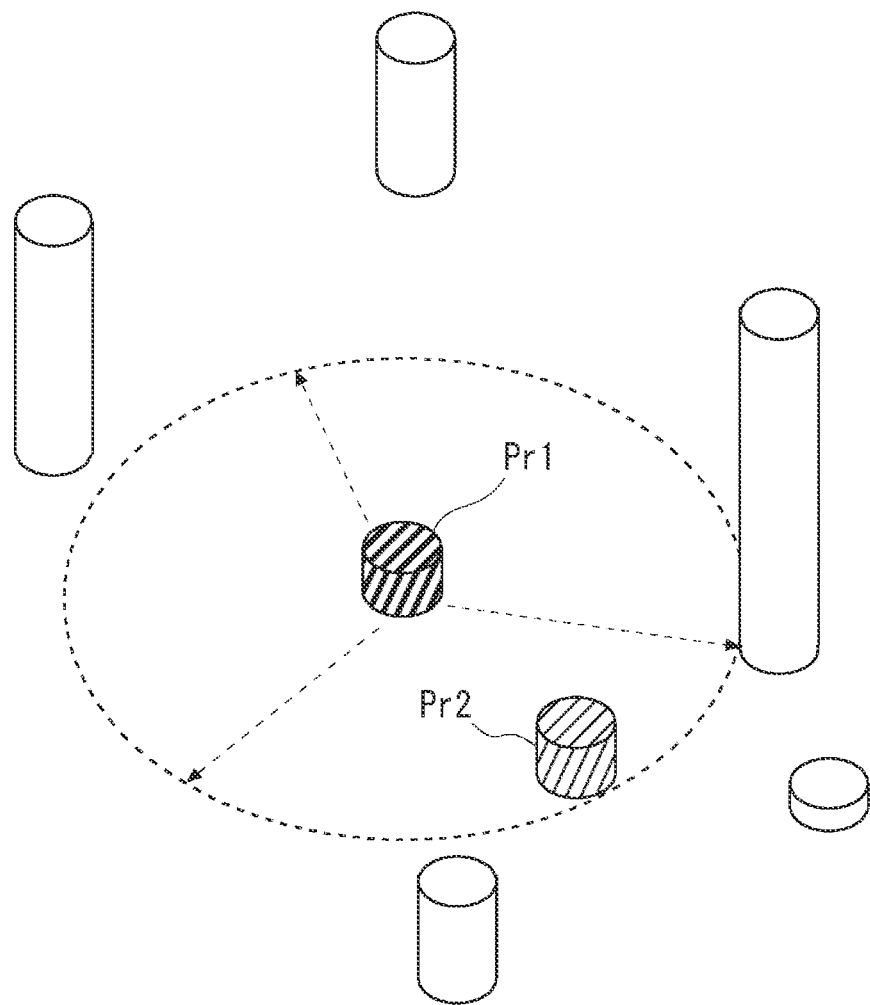
FIG. 3 is assignment of a first cluster.

FIG. 3 schematically shows an assignment of the first cluster. Here, a cluster different from the primary OTU is firstly assigned to each sample sequence. As a procedure of cluster assignment, firstly, a sample sequence to be a seed (hereinafter referred to as a seed sequence) is randomly selected from the whole sample sequences. Substantially, a primary OTU is randomly selected from the whole primary OTUs.

In one aspect shown in FIG. 3, a primary OTU (Pr1) is selected as the seed sequence. A circle of a broken line represents a range of similarity when viewed from the primary OTU (Pr1). Specifically, the circle represents a range having a similarity larger than or equal to a predetermined threshold value with the sequence of the primary OTU (Pr1). The first cluster is assigned to this range.

As shown in FIG. 3, the primary OTU (Pr1) and the different primary OTU (Pr2) are included in the similar range. Then, the first cluster is assigned to the primary OTU (Pr1) and the primary OTU (Pr2). Hatched columns indicate that the same cluster are assigned to the primary OTUs. These primary OTUs constitute one cluster. In other figures, the hatching indicates the same operation.

Although not illustrated in FIG. 3, in the same way, another cluster is also assigned to another primary OTU that is not similar to the primary OTU (Pr1). In the above way, the clusters including the primary OTUs are generated.

Figure 4:
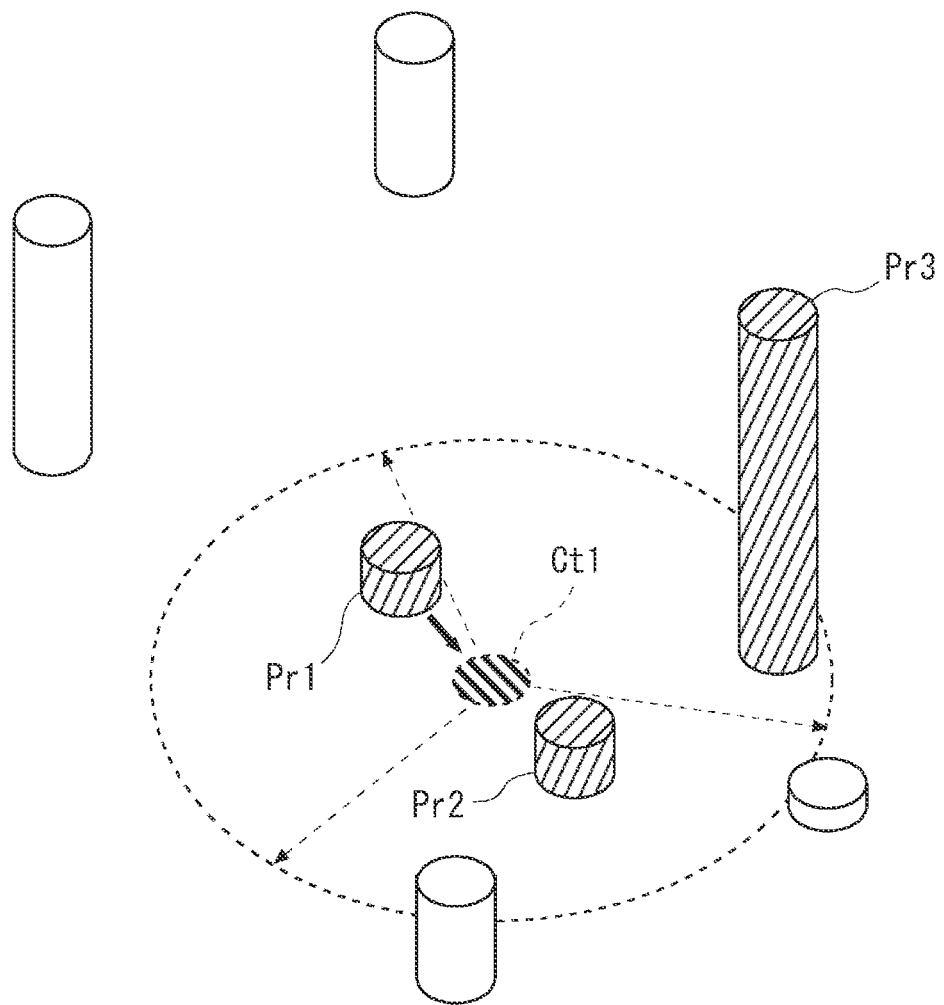
FIG. 4 is reassignment of a cluster.

FIG. 4 schematically shows the reassignment of clusters. A centroid Ct1 is the centroid of the cluster, specifically, the centroid between the primary OTU (Pr1) and the primary OTU (Pr2). The circle of the broken line represents a range of the similarity when viewed from the centroid Ct1. Specifically, the circle represents a range having a similarity larger than or equal to a predetermined threshold value with the sequence of the centroid Ct1. A cluster is reassigned to a primary OTU (Pr3) in a range similar to the newly generated centroid Ct1.

Figure 5:
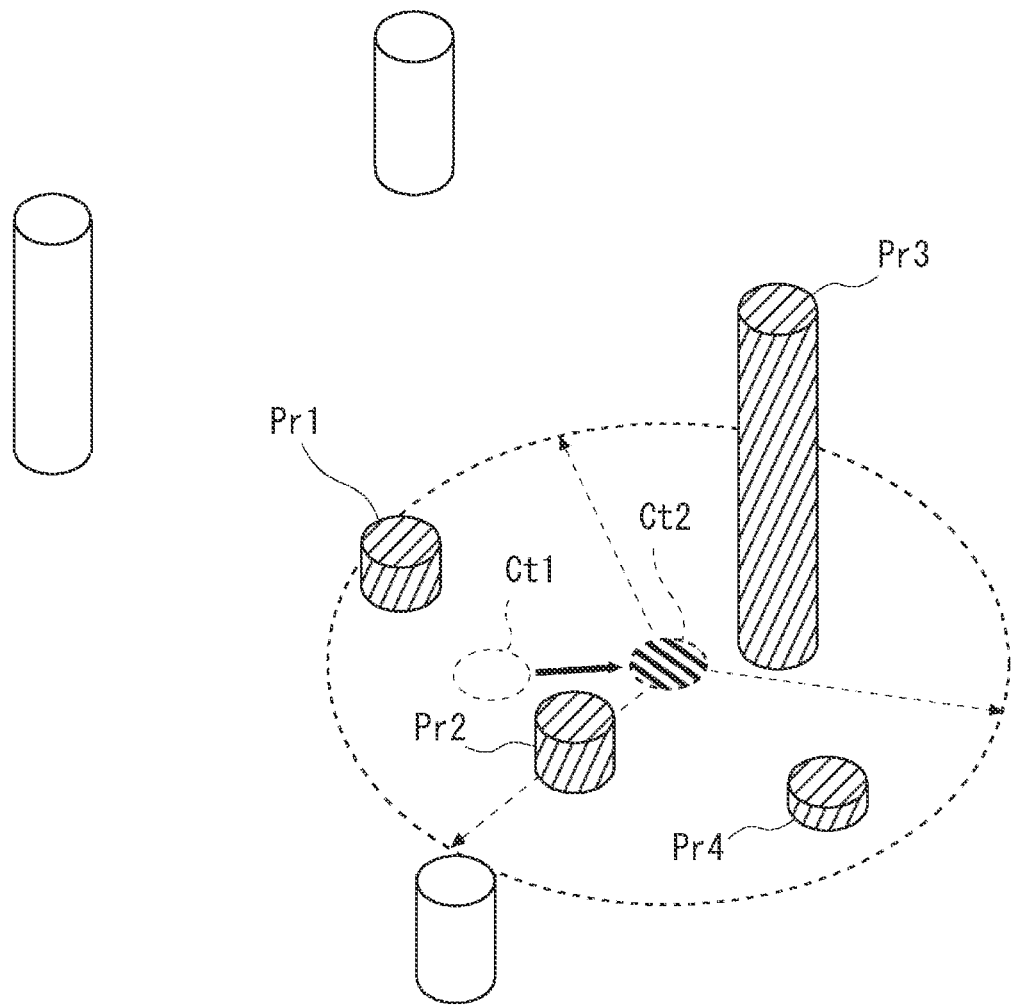
FIG. 5 is iteration of the assignment of the cluster.

FIG. 5 schematically shows an iteration of the assignment of a cluster. The centroid Ct2 is a centroid of the cluster having the primary OTU (Pr3), specifically, a centroid of the primary OTU (Pr1), the primary OTU (Pr2) and the primary OTU (Pr3). The circle of the broken line represents a range of similarity when viewed from the centroid Ct2. Specifically, the circle represents a range having a similarity larger than or equal to a predetermined threshold value with the sequence of the centroid Ct2. A cluster is reassigned to a primary OTU (Pr4) within a range similar to the newly generated centroid Ct2.

In the present embodiment, the reassignment of the cluster is iterated until the cluster converges. Thereby, a secondary OTU is generated.

Figure 6:
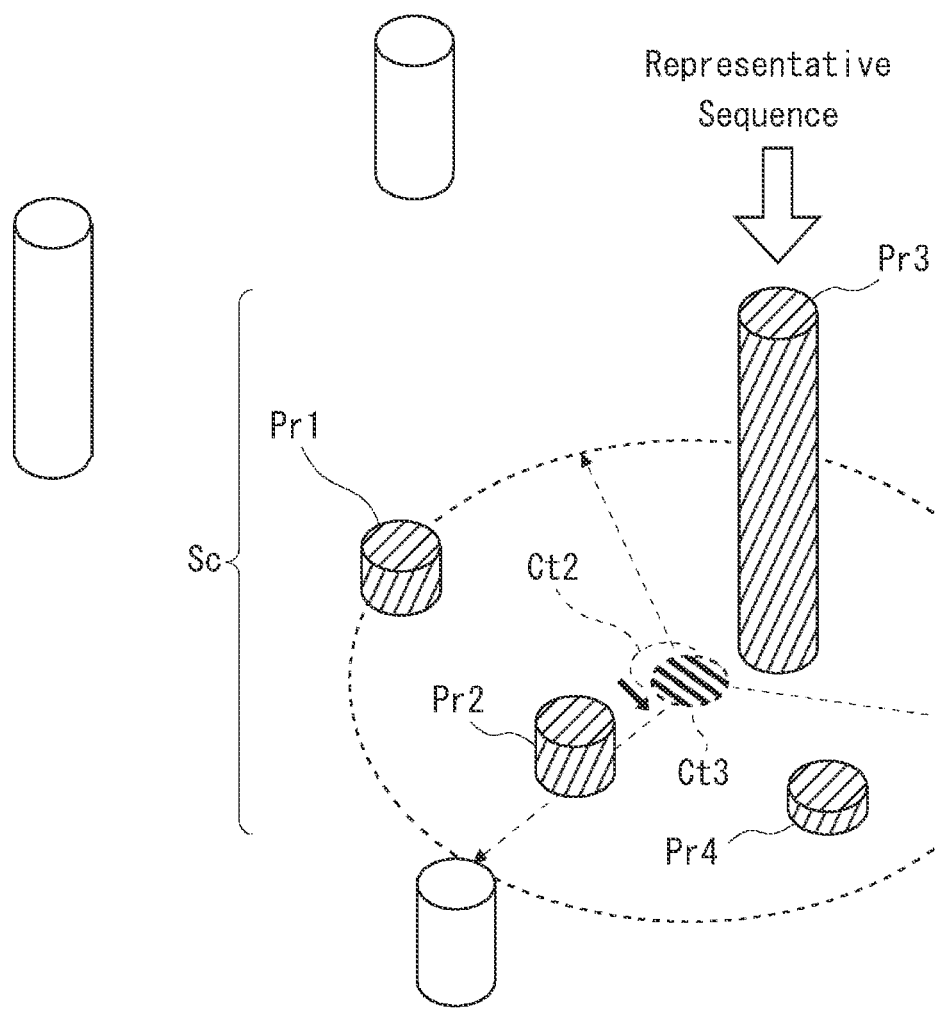
FIG. 6 is an identification of a representative sequence.

FIG. 6 schematically shows the identification of the secondary OTU (Sc) and the representative sequence. The centroid Ct3 is a centroid of the cluster having the primary OTU (Pr4), specifically, the centroid of the primary OTU (Pr1), the primary OTU (Pr2), the primary OTU (Pr3) and the primary OTU (Pr4). The circle of the broken line represents a range of the similarity when viewed from the centroid Ct3. Specifically, the circle represents a range having a similarity larger than or equal to a predetermined threshold value with the sequence of the centroid Ct3. Even though a cluster has been newly assigned to a range similar to the newly generated centroid Ct3, a combination of the primary OTUs constituting the cluster does not change. Accordingly, it is understood that the cluster has converged before the centroid Ct3 has been obtained.

The exploratory clustering is performed in the above way. The predetermined threshold value for the similarity in the exploratory clustering is less than 100%. In one aspect, the threshold value is an arbitrary value of 90% or larger. In one aspect, the threshold value is any one of 91, 92, 93, 94, 95, 96, 97, 97.5, 98, 98.5, 99 and 99.5%. When the threshold value is lowered, the analysis accuracy can be enhanced. When the threshold value is enhanced, the resolution can be enhanced. In addition, the calculation time can be reduced.

The cluster that is obtained as a result of the convergence of the exploratory clustering is an OTU. In the present embodiment, the cluster is referred to as a secondary OTU (Sc). Here, it should be noted that clusters obtained in the course of the exploratory clustering are also OTUs. The cluster which is composed of the firstly and randomly chosen seed and a sample sequence similar to the seed is an OTU.

The number of reassignments of clusters is one or more, which is performed before convergence. In the above embodiment, the reassignment is performed twice. This number of times becomes 3, 4, 5, 6, 7, 8 and 9 times, in some cases. In one aspect, an upper limit is provided on the number of reassignments. In one aspect, when the number of reassignments has reached an upper limit, the cluster is assumed to have converged.

In one aspect shown in FIG. 4 to FIG. 6, the sequence of the centroid of the cluster is a simple average of sequences of each primary OTU. In another aspect, the sequence of the centroid of the cluster is also an average of the sequences of each primary OTU, which is weighted by the number of sequences of each primary OTU.

It is allowed that at the time of the convergence, the primary OTU included in the secondary OTU is one. In addition, it is allowed that all the primary OTUs coincide with all the secondary OTUs.

In one aspect shown in FIG. 6, when all clusters including a cluster (not illustrated) have not been changed by the reassignment of clusters based on the centroid, it is assumed that the clusters have converged. In another aspect, when the amount of change in the combination of the primary OTUs in all the clusters is below a predetermined value, it is determined that convergence occurs.

In FIG. 3, the primary OTU (Pr1) was used as the seed. The first cluster has been determined from the seed. On the other hand, it is acceptable to determine a group formed of a plurality of primary OUTs that are randomly selected without consideration of the similarities of the sequences, as the first cluster.

In order to estimate the lineage in step S14 shown in FIG. 1, firstly, a representative sequence of each secondary OTU is selected. In one aspect, the sequence of the primary OTU which has the largest number of sequences among the primary OTUs included in each secondary OTU is set to be the representative sequence of the secondary OTUs. In one aspect shown in FIG. 6, the primary OTU (Pr3) has the largest number of sequences among the secondary OTUs (Sc). Accordingly, the representative sequence of the secondary OTUs (Sc) is set to be the sequence of the primary OTU (Pr3).

In step S14 shown in FIG. 1, the representative sequence is further collated with a database. In the above way, the lineage of the secondary OTU is estimated. In one aspect, the lineage estimation is to estimate the taxa of any of the phylum, class, order, family, genus, species, and subspecies of the bacterium of the secondary OTU.

In one aspect, the database is a public database. In another aspect, the database is a database which has been generated by meta-analysis of one or more other databases. In one aspect, the database is connected to a computer via a network.

At the time of meta-analysis, sequences in other databases are distinguished, for example, between sequences which are correctly annotated and sequences which are not correctly annotated. In one aspect, the correctly annotated sequence is a sequence of a type strain (Type Strain). In one aspect, caution is necessary so that a plurality of identical sequences are not included in the database which has been generated by the meta-analysis. Due to such optimization of the database, a calculation cost at the time when the representative sequence is collated with the database can be greatly reduced. In one aspect, calculation is performed on only top hit.

EXAMPLE

Figure 7:
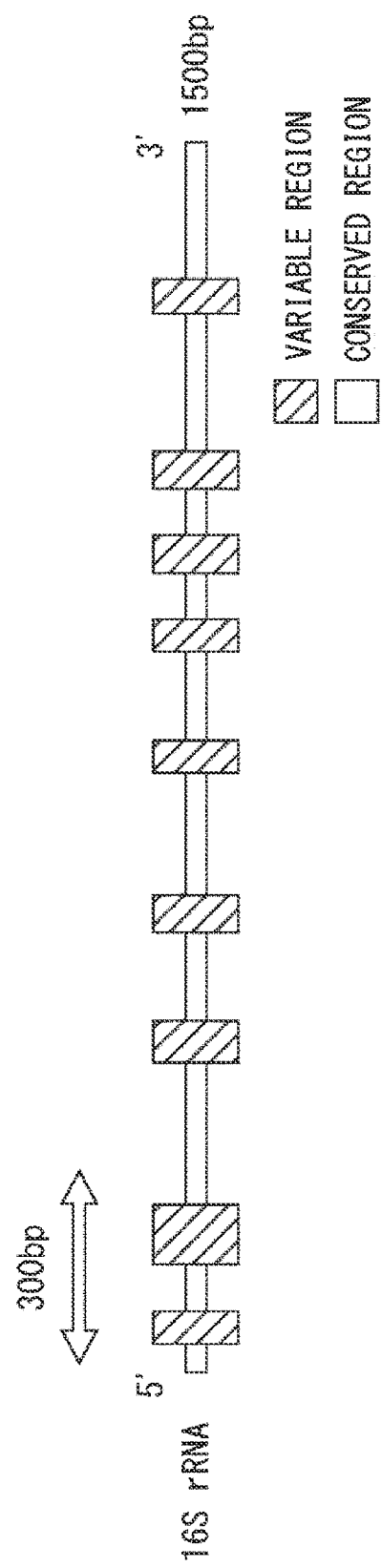
FIG. 7 is a 16S rRNA gene.

FIG. 7 schematically represents a 16S rRNA gene having a base length of approximately 1500 bp. In this Example, a DNA having a partial sequence of the 16S rRNA gene is used as a sample. The 16S rRNA gene has nine hypervariable regions (hereinafter referred to as variable regions), and regions existing among these regions (hereinafter referred to as conserved regions). The partial sequence is composed of a region of 300 bp, which includes two variable regions on the 5' side.

In the present Example, a DNA having the above partial sequence is cloned from the intra-uterine fluid or the vaginal swab of a subject. A unique bacterial flora is contained in these swabs. The obtained DNA is used as a sample and is subjected to DNA sequencing, and a sample sequence is obtained. The DNA sequencing is performed by use of a next generation sequencer.

The number of sequences output from the next-generation sequencer is very large. Due to the above clustering, it becomes unnecessary to search the homology for all sequences in the database. In one viewpoint, this is because due to the homology searching of the representative sequence, the lineages can be estimated for all sample sequences in the secondary OTU.

Figure 8:
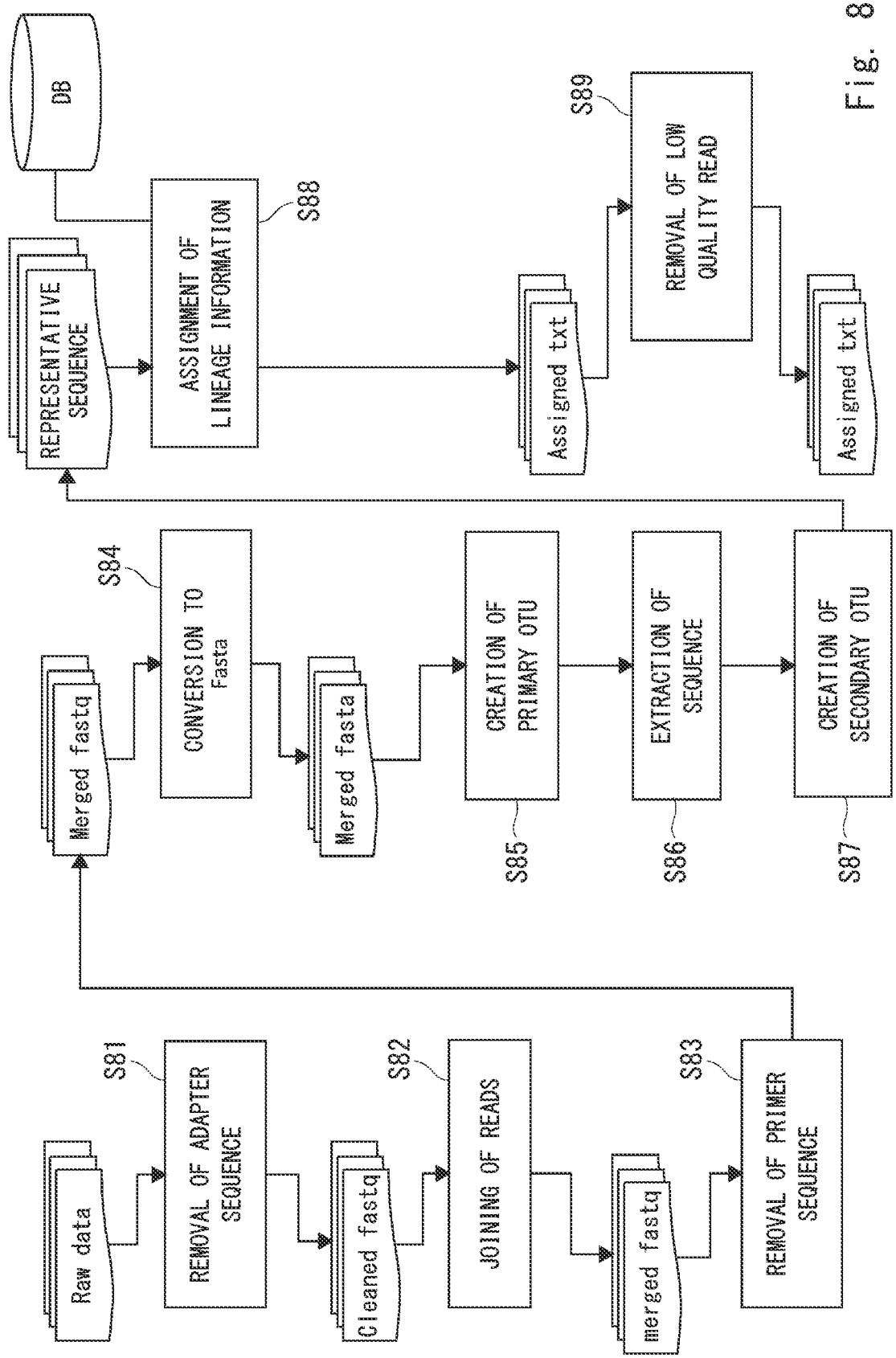
FIG. 8 is a flow of Example.

FIG. 8 shows a flow of the metagenomic analysis after the sequences have been determined. Firstly, in step S81, adaptor sequences are removed from raw data (Raw Data) of the sequence, and thereby, a clean FASTQ format of data (Cleaned fastq) is obtained. The program name Trimmomatic is available. The present data and each of the following data include an identifier of the subject.

In step S82 shown in FIG. 8, the reads in the FASTQ format of data are combined, and thereby, a combined FASTQ format of data (merged fastq) is obtained. The program name fastq-join is available.

In step S83 shown in FIG. 8, the primer sequence in the FASTQ format of data is removed. Furthermore, in step S84, the FASTQ format of data is converted into a FASTA format of data. The program name PRINSEQ is available in these operations.

In step S85 shown in FIG. 8, a primary OTU is created from sample sequences contained in the FASTA format of data. UCLUST of the program name Qiime pick otus.py is available. A threshold value for the similarity (similarity) is set to be 1.00 (100%). Furthermore, in step S86, information of the sequence is extracted from each primary OTU. The program name Qiime pick rep set.py is available.

In step S87 shown in FIG. 8, the secondary OTU is created from the sample sequence. The program name Qiime pick otus.py is available. The threshold value for the similarity (similarity) is set to 0.995 (99.5%). Furthermore, a primary OTU having the largest number of sequences is selected from the primary OTUs included in the secondary OTUs, and the sequence is set to be the representative sequence.

In the present Example, the UCLUST of the Qiime pick otus.py is used for exploratory clustering. In another aspect, the exploratory clustering is performed on a platform other than UCLUST. Examples of such platforms include usearch, CD-HIT and vsearch.

In Step S88 shown in FIG. 8, the representative sequence is collated with the database (DB), and thereby, data (Assigned txt) is generated in which the lineage information is assigned to each secondary OTU. The program name BLAST is available. Furthermore, in step S89, reads having a low quality are removed from the data.

The database (DB) to be used in the present Example contains sequences and annotations of the 16S rRNA gene of genus *Lactobacillus*. In another aspect, the database further includes sequences and annotations of the 16S rRNA genes of genus *Bifidobacterium*, genus *Propionibacterium*, genus *Gardnerella*, genus *Streptococcus*, and genus *Veillonella*. In such an aspect, the above partial subsequences are not completely conserved among these bacterial genera. In one aspect, the above partial sequence is a sequence of a portion of which the preserving property is low, in the whole sequences of the 16S rRNA. In one aspect, the preserving property of the above partial sequence is low in such a degree that these bacterial genera can be distinguished.

Examples of other databases are NCBI, GreenGenes, SILVA, EzBioCloud, and the Ribosomal Database Project. In another aspect, the database is a database which has been generated by meta-analysis of another database. Examples of other databases are the databases exemplified above. The examples of the databases exemplified above and databases generated by meta-analysis of those examples may include chimera and misannotation. As described above, due to the partial sequence of the 16S rRNA gene being used, the influence of the chimera and the misannotation can be made smaller than the time when a full-length sequence has been used. In addition, a calculation cost can be reduced as compared with the time when the full-length sequence has been used.

Figure 9:
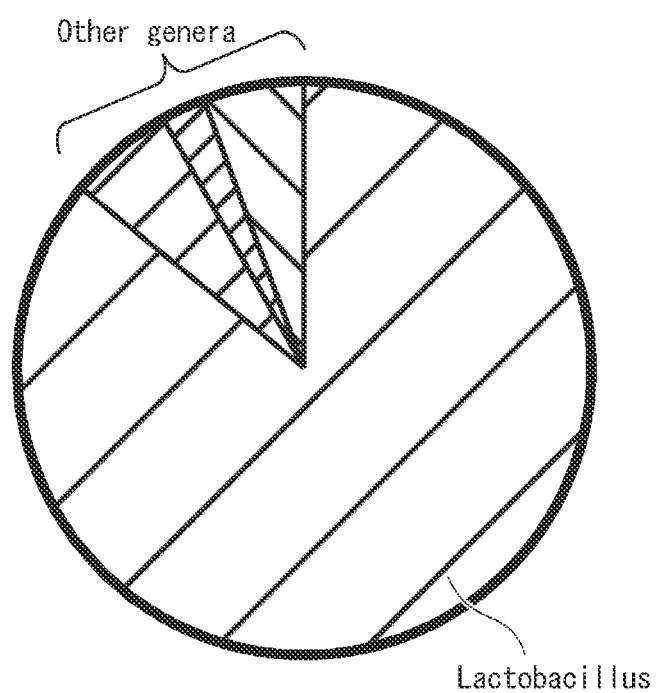
FIG. 9 is a composition ratio of bacteria.

From the obtained data (Assigned txt), the data is obtained which contains a composition ratio of bacteria in the bacterial flora and the identifier of the subject. In one aspect, the composition ratio of the bacteria is proportional to the number of sequences of the secondary OTU. The secondary OTUs are annotated with the taxonomy of the bacteria. In one aspect, the composition ratio of bacteria is, for example, a composition ratio in a bacterial flora of the genus *Lactobacillus* and a genus of a bacterium other than the genus *Lactobacillus* as shown in FIG. 9.

In one aspect, a computer provides the composition ratio of the bacteria and the identifier of the subject to a diagnostician. In one aspect, the information is provided via a server and a terminal of the diagnostician which are connected via a network. The diagnostician diagnoses ease of pregnancy by in-vitro fertilization or ease of pregnancy by natural pregnancy of the subject, based on the composition ratio of the bacterial flora.

Reference Example 1

Figure 10:
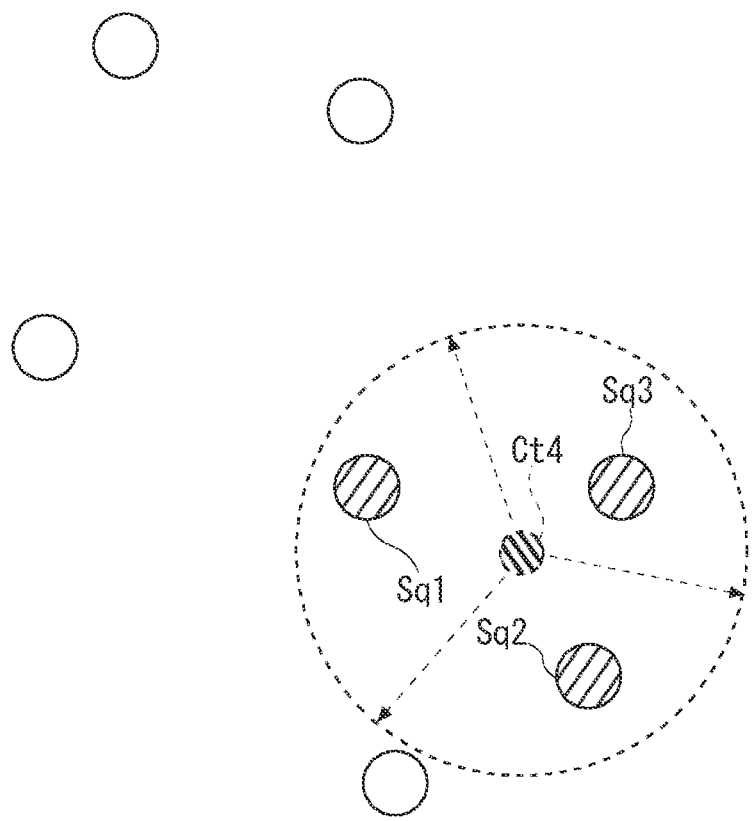
FIG. 10 is clustering in Reference Example.

FIG. 10 shows the case where the primary OTU was not created and the sample sequence was subjected to the exploratory clustering. A centroid Ct4 is similar to sequences Sq1, Sq2 and Sq3 that constitute the cluster. However, the centroid Ct4 is a pseudo sequence. In other words, the sequence is a sequence which is not contained in the sample.

When the centroid Ct4 shown in FIG. 10 is compared with the database, and thereby the lineage of the OTU is estimated, there is a possibility that the lineage is erroneously estimated. This tendency is particularly remarkable in the 16S rRNA gene in which the preserving property is high across the whole of the taxonomy of bacteria. In other words, this method tends to cause the misannotation. Accordingly, it is preferable to set the threshold value to about 97%. Such a threshold value is suitable for estimating the lineage of bacteria in a genus or a taxonomy larger than the genus.

In contrast to this, the above embodiment is common to the above embodiment in that the exploratory clustering is used. However, the method selects the representative sequence from the sequences of the primary OTUs in the secondary OTU, and accordingly, it does not occur to estimate the lineage with the use of the pseudo sequence. Because of this, the method can reduce the influence of the pseudo sequence. In addition, in the above embodiment, the method can incorporate also a sample sequence in which an error has occurred in the DNA sequencing, into a secondary OTU. Accordingly, the number of sequences contained in the secondary OTU satisfactorily represents a substance of the sample or the bacterial flora. In the metagenomic analysis of the above embodiment, the lineage can be more finely estimated than in the metagenomic analysis in which only the exploratory clustering is performed.

It should be noted that errors in sequencing are also the background of the cause by which primary OTUs in which the sequences are similar to each other are formed. For example, in the case shown in FIG. 2, it may be considered that an OTU a is composed of a sample sequence having a true sequence, and an OTU b and an OTU c are composed of sample sequences containing errors. In FIG. 3 to FIG. 6, secondary OTUs are created while also sample sequences containing errors are incorporated. However, this operation creates the representative sequence from the primary OTU having the largest number of sequences, and accordingly, can enhance the accuracy of lineage estimation of bacteria.

It is also acceptable to generate an OTU according to the method of the present Reference Example, and generate a sub-OTU based on a sample sequence having 100% similarity in the OTU. It is also acceptable to set the sequence of the sub-OTU that has the largest number of sequences among such sub-OTUs, as the representative sequence. In other words, it is also acceptable to reverse the order of the generation of the primary OTU and the generation of the secondary OTU in the above embodiment.

According to the above embodiment, it is preferable to generate the secondary OTU after having generated the primary OTU. Thereby, it is possible to omit redundant calculation of completely coinciding sequences in the primary OTUs, in the generation of the secondary OTU.

Reference Example 2

In the above embodiment, the primary OTU and the secondary OTU are created with the use of a non-hierarchical clustering method called exploratory clustering, and thereby, the accuracy of clustering and the calculation cost are balanced. As an example of a method different from this non-hierarchical clustering method, such a method is exemplified as to generate OTUs by clustering the sample sequences by hierarchical clustering, without using a stepwise method of generating the primary OTUs and the secondary OTUs.

Examples of the hierarchical clustering include Single linkage, Complete linkage and Average linkage. In a case where the stepwise method of generating the primary OTU and the secondary OTU is not used, the OTU becomes very large in the Single linkage, and accordingly, it is difficult to enhance the accuracy. When the stepwise method is not used, a large amount of small OTUs are generated, in the Complete linkage. Accordingly, the calculation cost is required for collation with the database. When the stepwise method is not used, OTUs can be generated which have an appropriate size and an appropriate number, in the Average linkage. However, the stepwise method is not used, and thereby, the calculation cost itself required for the hierarchical clustering becomes very high. In addition, in any of the hierarchical clustering methods, in the case where the stepwise method is not used, when the centroid is selected as the representative sequence, the representative sequence often becomes a pseudo sequence.

The stepwise method of generating the primary OTUs and the secondary OTUs with the use of the exploratory clustering which is used in the above embodiment is excellent in the balance between the accuracy and the calculation cost, as compared with the method of generating the OTUs in one step with the use of the hierarchical clustering. In the above embodiment, the representative sequence is selected from the primary OTUs in the secondary OTU, and accordingly, it does not occur to estimate the lineage with the use of the pseudo sequence. Because of this, the influence of the pseudo sequence can be reduced.

It should be noted that the present invention is not limited to the above embodiment and can be appropriately modified without departing from the scope of the invention.

In the above embodiment, a meta 16S analysis was performed over each genus. In another viewpoint of the present invention, a 16S ribosomal gene and an ITS (Internal Transcribed Spacer) between 23S ribosomal genes are used for the clustering of bacteria.

In another aspect, a range of the metagenomic analysis may be narrowed down into a particular genus. In the one aspect, recA, rpoB and other housekeeping genes are used in place of the 16S ribosomal gene. In addition, it is also acceptable to combine a plurality of these housekeeping genes and perform MLSA (Multilocus sequence typing).

In the above embodiment, the metagenomic analysis of the bacterial flora was performed. Another viewpoint of the present invention is the metagenomic analysis of the microbial flora including eukaryotes such as protists and fungi. For the clustering of the eukaryotes, an 18S ribosomal gene and the ITS (Internal Transcribed Spacer) in a ribosomal DNA of the eukaryote can be used.

In the above embodiment, the exploratory clustering was used as the clustering based on a threshold value for the similarity between sequences. In another viewpoint of the invention, the hierarchical clustering is used as the clustering based on a threshold value for the similarity between sequences. In one aspect, the hierarchical clustering is any of Single linkage, Complete linkage and Average linkage. In another aspect, the hierarchical clustering utilizes a cluster command in the analysis package mothur <https://mothur.org/wiki/cluster/>. In one aspect, base sequences having 100% similarity in a sample sequence are grouped with each other, by the mothur, and thereby, primary OTUs (Operational Taxonomic Unit) are generated. Next, a cluster is assigned to sample sequences that have a similarity larger than or equal to a predetermined threshold value with the sequence of the centroid of the cluster, by the hierarchical clustering of the mothur. Here, the predetermined threshold value is less than 100%. Next, the sequence of the primary OTU having the largest number of sequences among the primary OTUs included in each secondary OTU is set as the representative sequence of the secondary OTU, then, the representative sequence is collated with the database, and the lineage of the secondary OTU is estimated. In this way, when the primary OTU and the secondary OTU are generated, even in the case where the hierarchical clustering is used, the influence of the pseudo sequence can be reduced.

It is also acceptable to use the exploratory clustering for the generation of the secondary OTU, after having used the hierarchical clustering for the generation of the primary OTUs. It is also acceptable to use the hierarchical clustering for the generation of the secondary OTU, after having used the exploratory clustering for the generation of the primary OTUs.

In addition to the UCLUST and the mothur described above, various types of exploratory clustering and hierarchical clustering can be used as the clustering based on a threshold value for the similarity between sequences. In another aspect, blast, prefix/suffix, Trie, uclust_ref, usearch_ref, usearch61, sumaclust, sortmerna_v2, and swarm are used which are listed in <http://qiime.org/scripts/pick_otus.html>.

Another viewpoint of the present invention is a program for causing a computer to execute processing relating to the above metagenomic analysis. Another viewpoint of the present invention is a disk, a tape, a flash memory and other non-volatile storage media, which store the above program therein. Another viewpoint of the present invention is to provide the above program for download via a network. Another viewpoint of the present invention is to receive a request via a network, execute the above program on a computer in response to the request, and provide a processing result via the network in response to the request. In one aspect, a plurality of apparatuses connected via a network execute an operation of a computer which executes a program.

This application claims priority based on Japanese Patent Application No. 2021-36093 filed on Mar. 8, 2021, and the entire disclosure thereof is incorporated herein.

REFERENCE SIGNS LIST

Ct1-4 CENTROID, DB DATABASE, Pr1 to 4 PRIMARY OTU, S11 to 14 STEP, S81 to 89 STEP, Sc SECONDARY OTU, Sq1 to 3 SEQUENCE

The invention claimed is:

1. A method of a metagenomic analysis of a bacterial flora, comprising:
performing clustering on base sequences obtained by DNA sequencing of a sample containing the bacterial flora, which will be hereinafter referred to as a sample sequence, wherein the clustering comprises
grouping base sequences having 100% similarity with each other, for the sample sequences thereby to generate a primary OTU (Operational Taxonomic Unit); and
performing the clustering on the sample sequences thereby to generate a secondary OTU composed of a sequence of a predetermined centroid, and sample sequences that have a similarity larger than or equal to a predetermined threshold value with the sequence of the centroid, on condition that the predetermined threshold value is less than 100%, and
setting a sequence of a primary OTU having a largest number of sequences among the primary OTUs included in each secondary OTU, as a representative sequence of the secondary OTU, collating the representative sequence with a database, and thereby estimating a lineage of the secondary OTU.

2. The method according to claim 1, further comprising:
at the time when generating the secondary OTU, iterating operations of:
firstly assigning a cluster different from the primary OTUs to the sample sequences; and
further reassigning the cluster to a sample sequence having a similarity larger than or equal to a predetermined threshold value with the sequence of the centroid of the cluster, until convergence.

3. The method according to claim 2, wherein firstly assigning the cluster to the sample sequence comprises:
randomly selecting a seed sequence from the sample sequence; and
also assigning a first cluster to the seed sequence and a sequence having a similarity larger than or equal to the predetermined threshold value or larger with respect to the seed sequence.

4. The method according to claim 2, wherein
when the secondary OTU is generated after the primary OTU has been created,
the cluster is a cluster including the primary OTU; and
the sequence of the centroid is an average obtained by weighting the sequences of the primary OTUs with the number of sequences of the primary OTUs.

5. The method according to claim 2, wherein when the cluster reassignment has been performed and an assignment of all clusters have not changed, the all clusters is determined that convergence occurs.

6. The method according to claim 1, wherein
the sample is an intra-uterine fluid or a vaginal swab of a subject;
the sample sequence is generated by DNA sequencing of a partial sequence of a 16S rRNA gene of genomic DNAs extracted from the sample;
the database includes a sequence and an annotation of the 16S rRNA gene of genus *Lactobacillus*;
in the lineage estimation, a genus of a bacterium of the secondary OTU is estimated; and
data is generated which includes an identifier of the subject and a composition ratio of genera of bacteria containing the genus *Lactobacillus* in the bacterial flora.

7. The method according to claim 6, wherein
the database further comprises sequences and annotations of 16S rRNA genes of genus *Bifidobacterium*, genus *Propionibacterium*, genus *Gardnerella*, genus *Streptococcus*, and genus *Veillonella*; and
the partial sequence is a sequence of a portion in the whole sequences of the 16S rRNA genes, which is not completely conserved among these bacterial genera.

8. The method according to claim 6, wherein
the database is a database generated by a meta-analysis of a plurality of other databases.

9. A method for diagnosing ease of pregnancy of a subject, comprising:
collecting an intra-uterine fluid or a vaginal swab from the subject as a sample;
metagenomically analyzing the sample by the method according to claim 1, wherein
the sample sequences are generated by DNA sequencing of a partial sequence of a 16S rRNA gene of genomic DNAs extracted from the sample, and
the database includes sequences and annotations of the 16S rRNA gene of genus *Lactobacillus*;
in the lineage estimation, estimating a genus of a bacterium of a secondary OTU; and
diagnosing ease of pregnancy of the subject, based on a composition ratio of genus *Lactobacillus* to genera of bacteria other than genus *Lactobacillus* in a bacterial flora.

10. A method of a metagenomic analysis of a microbial flora of a eukaryote, comprising:
performing clustering on base sequences obtained by DNA sequencing of a sample containing the microbial flora, which will be hereinafter referred to as a sample sequence, wherein the clustering comprises
grouping base sequences having 100% similarity with each other, for the sample sequences, thereby to generate a primary OTU (Operational Taxonomic Unit), and
performing the clustering on the sample sequences thereby to generate a secondary OTU composed of a sequence of a predetermined centroid, and sample sequences that have a similarity larger than or equal to a predetermined threshold value with the sequence of the centroid, on condition that the predetermined threshold value is less than 100%; and setting a sequence of a primary OTU having a largest number of sequences among the primary OTUs included in each secondary OTU, as a representative sequence of the secondary OTU, collating the representative sequence with a database, and thereby estimating a lineage of the secondary OTU.

11. A non-transitory computer-readable medium storing a program for a metagenomic analysis of a microbial flora of bacteria or eukaryotes, the program being configured to:

cause a computer to perform clustering on base sequences obtained by DNA sequencing of a sample containing the microbial flora, which will be hereinafter referred to as a sample sequence, wherein the clustering comprises grouping base sequences having 100% similarity with each other, for the sample sequences thereby to generate a primary OTU (Operational Taxonomic Unit), and performing the clustering on the sample sequences thereby to generate a secondary OTU composed of a sequence of a predetermined centroid, and sample sequences that have a similarity larger than or equal to a predetermined threshold value with the sequence of the centroid, on condition that the predetermined threshold value is less than 100%; and set a sequence of a primary OTU having a largest number of sequences among the primary OTUs included in each secondary OTU, as a representative sequence of the secondary OTU, causing the computer to collate the representative sequence with a database, and thereby causing the computer to estimate a lineage of the secondary OTU.

\* \* \* \* \*